United States Patent [19]

Carter

[11] Patent Number: 4,863,470
[45] Date of Patent: Sep. 5, 1989

[54] IDENTIFICATION MARKER FOR A BREAST PROSTHESIS

[75] Inventor: Garry L. Carter, Racine, Wis.

[73] Assignee: Medical Engineering Corporation, Racine, Wis.

[21] Appl. No.: 102,752

[22] Filed: Sep. 24, 1987

Related U.S. Application Data

[63] Continuation of Ser. No. 713,517, Mar. 19, 1985, abandoned.

[51] Int. Cl.⁴ ............................................. A61F 2/12
[52] U.S. Cl. ................................. 623/8; 623/11
[58] Field of Search ................. 623/8, 7, 11, 16; 128/92 VZ

[56] References Cited

U.S. PATENT DOCUMENTS

| | | | |
|---|---|---|---|
| 3,293,663 | 12/1966 | Cronin | 3/36 |
| 3,341,417 | 9/1967 | Sinaiko | 128/654 |
| 3,915,162 | 10/1975 | Miller | 128/92 YE |
| 4,636,213 | 1/1987 | Pakiam | 623/8 |

*Primary Examiner*—Richard J. Apley
*Assistant Examiner*—David J. Isabella
*Attorney, Agent, or Firm*—Stuart E. Krieger

[57] ABSTRACT

A radiopaque identification marker is incorporated into a radiolucent prosthesis, such as a breast implant. The marker denotes data which is ascertainable prior or subsequent to implantation.

10 Claims, 1 Drawing Sheet

IDENTIFICATION MARKER FOR A BREAST PROSTHESIS

This is a continuing application of application Ser. No. 713,517 filed Nov. 19, 1985 titled "Identification Marker for a Breast Prosthesis", now abandoned.

FIELD OF THE INVENTION

This invention relates to prostheses and more particularly to an identification marker incorporated into a breast prosthesis.

BACKGROUND OF THE INVENTION

Mammary prostheses or implants must be available in numerous sizes to replicate the wide range of breast sizes of female patients. In order to reduce the possibility of confusion in the operating room, it is preferable that the implant's size be readily ascertainable after it has been separated from its packaging. At the present time, the size of the implant can be determined by direct measurement, or it can be marked with lettering which indicates its size. The former means of determining an implant's size can be awkward and time consuming. The latter technique has been found relatively successful when direct viewing of the implant is possible; however, there remains a need for the ability to determine the size of an implant after it has been implanted into a patient. In such a situation, the letter markings on the implant which are presently in use are inadequate since they cannot be read when the implant is in the body.

Similarly, other types of implants, including penile, bladder and incontinence devices, would benefit from being readily identifiable both prior and subsequent to implantation.

It is therefore an object of the present invention to provide an implant with a tab or marker which indicates the size of the implant in the absence of its packaging and without the need for measuring devices.

It is also an object of the present invention to provide an implant with a marker which facilitates the determination of the size of an implant after it has been implanted.

It is a further object of the present invention to provide an implant which provides identifying information that is ascertainable both prior and subsequent to implantation.

SUMMARY OF THE INVENTION

In accordance with these and other objects there is provided by the present invention a prosthesis for subcutaneous implantation which includes a container having a radiolucent portion surrounding a radiopaque identification marker. The identification marker is visible and easily readable by eye prior to implantation and readable from an x-ray photograph of the prosthesis after implantation.

Preferably, the prosthesis is a breast implant which has a radiolucent silicone elastomeric shell containing a radiolucent silicone gel and a radiopaque identification marker within the gel. Other implants or prostheses, such as penile, artificial bladder and incontinence devices, may also incorporate the identification marker advantageously.

DESCRIPTION OF THE DRAWINGS

Other objects and advantages will become apparent to those skilled in the art when the following detailed description is read in conjunction with the accompanying drawings, wherein.

DESCRIPTION OF THE PREFERRED EMBODIMENT

Referring now to the Figs. wherein a mammary implant or prosthesis generally designated by the numeral 10 includes a shell 12 filled with a gel 14. The shell 12 is made of a radiolucent material, preferably a silicone (polymeric) elastomer. Suitable shell materials include organo siloxane copolymers of the type set forth in U.S. Pat. No. 3,665,520. The gel 14 which fills the shell 12 is also radiolucent and is preferably a silicone gel. A particularly suitable gel 14 is a liquid methyl silicone resin capable of being vulcanized blended with a dimethyl silicone fluid. Other suitable mammary prostheses which comprise flexible shells of a silicone polymer filled with a silicone gel are well-known in the art, see e.g. U.S. Pat. No. 3,293,663 to Cronin.

Figure 1:
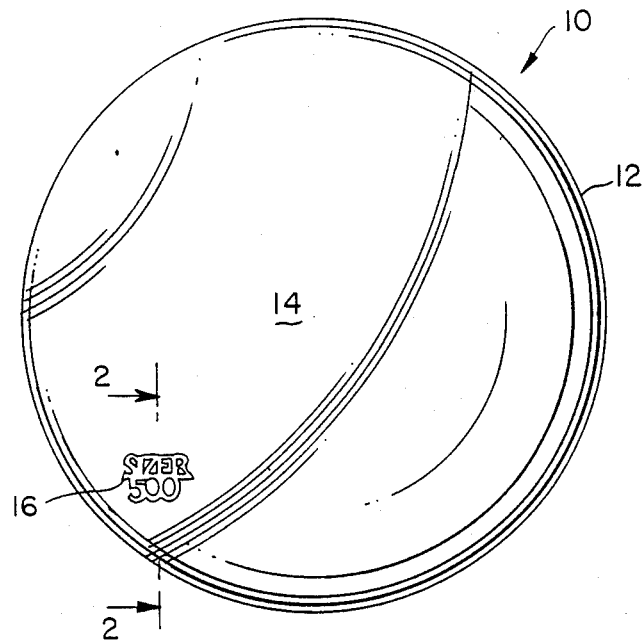
FIG. 1 is a top plan view of a mammary prosthesis which incorporates a marker in accordance with the present invention.
Figure 2:
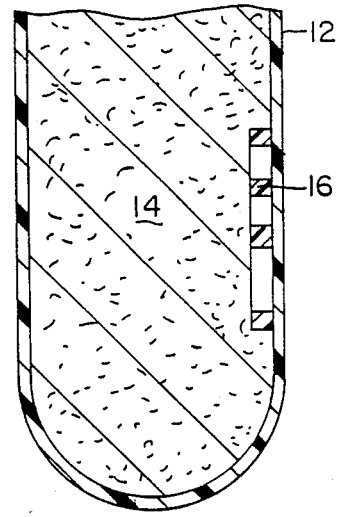
FIG. 2 is a cross-sectional taken along line 2—2 of FIG. 1.

The implant 10 includes within the shell 12 an identification marker or tab 16 which denotes the size of the implant 10. The tab 16 is made from material which is radiopaque, such as silicone with bismuth trioxide or silicone with barium sulfate. As shown most clearly in FIG. 1, the tab 16, which is formed preferably by molding, reads "SIZER 500" signifying that this prosthesis has a volume of 500 cubic centimeters. Clearly, this tab 16 can be molded or shaped, prior to insertion within the container, so as to provide other or additional identifying information, for example the manufacturer, year of manufacture, and type of prosthesis. Any information considered appropriate for retrieval prior to or after implantation can be coded into the tab 16. Information concerning the implanted prosthesis can subsequently be obtained by x-ray of the implanted prosthesis 10 without resorting to surgery or autopsy.

The identification tab 16 is inserted into the gel-filled shell 12 prior to the sealing of the shell 12. The high viscosity of the gel 14 retards movement of the tab so that the tab 16 can be manually positioned and naturally retained within the shell 12 in an orientation easily recordable on an x-ray plate. Alternatively, the tab 16 can be affixed with an adhesive to the interior of the shell 12.

Figure 3:
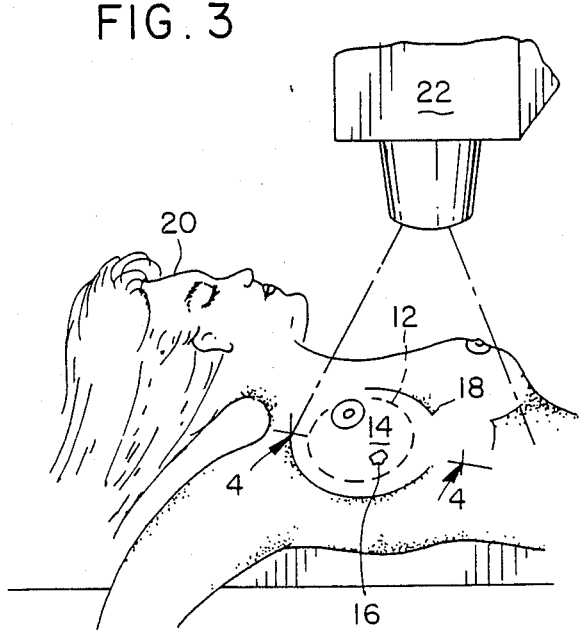
FIG. 3 is a schematic view of an x-ray being taken of the mammary prosthesis of FIG. 1 implanted in the breast of a female patient.
Figure 4:
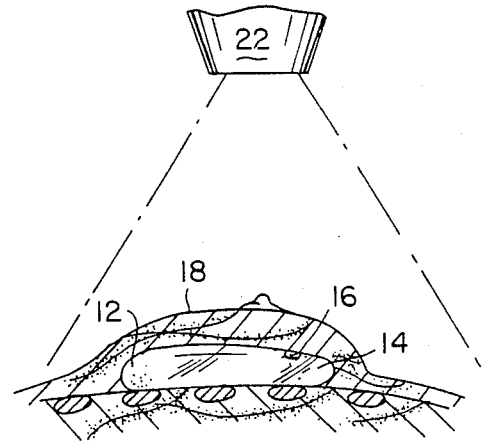
FIG. 4 is a cross-sectional view taken along line 4—4 of FIG. 3.

Once a prosthesis 10 incorporating the size identifying tab 16 is separated from its packaging, the size of the prosthesis 10 can be readily ascertained prior to implantation since the tab 16 is readily visible. After the prosthesis is implanted within the patient's breast 18, a physician or other medical personnel can readily ascertain the size of the implant 10 upon x-ray of the patient 20 with standard x-ray equipment 22, as shown in FIGS. 3 and 4. Consequently, the size of the implant 10 can be readily determined either before or after the implantation of the prosthesis.

I claim:

1. A prosthesis for subcutaneous implantation in a patient comprising:

a container suitable for implantation, said container being at least partly transparent and having a radiolucent portion; and a radiopaque identification marker at least partly surrounded by said radiolucent portion, said marker including alphanumeric symbols that are visible and readable by eye through said transparent part of said container prior to implantation and readable after implantation from an x-ray photograph of the patient.

2. The prosthesis of claim 1 wherein said container includes a radiolucent outer shell and a radiolucent material encased within said shell, said marker being at least partly surrounded by said radiolucent material.

3. The prosthesis of claim 1 wherein said container is suitably shaped for implantation in a patient's breast, said shell is a silicone elastomer and said material is a silicone gel.

4. The prosthesis of claim 2 wherein said identification marker is made of silicone with bismuth trioxide.

5. The prosthesis of claim 3 wherein said identification marker is made of silicone with barium sulfate.

6. The prosthesis of claim 3 wherein said identification marker is secured to an inner wall of said shell.

7. The prosthesis of claim 3 wherein said identification marker is substantially fixed in position within said silicone gel.

8. A mammary prosthesis for subcutaneous implantation in a patient comprising:

a radiolucent and transparent silicone elastomer shell;

a radiolucent and transparent silicone gel contained within said shell; and a radiopaque identifying marker within said gel, said marker including alphanumeric symbols that are readable by eye through said transparent shell and gel prior to implantation and readable after implantation from an x-ray photograph of the patient.

9. The prosthesis of claim 3 wherein said gel has a high viscosity so as to enable said identification marker to be located in a fixed position in said gel.

10. The prosthesis of claim 3 wherein said identification marker is shaped to indicate the prosthesis size.

* * * * *